United States Patent
Schott et al.

(10) Patent No.: US 11,517,774 B2
(45) Date of Patent: *Dec. 6, 2022

(54) COMPOSITIONS COMPRISING SOLVENT, A MONOALCOHOL AND GLYCERIN

(71) Applicant: L'OREAL, Paris (FR)

(72) Inventors: Andrea E. Schott, Summit, NJ (US); Aline Aude Guimont, South Orange, NJ (US)

(73) Assignee: L'OREAL, Paris (FR)

( * ) Notice: Subject to any disclaimer, the term of this patent is extended or adjusted under 35 U.S.C. 154(b) by 96 days.

This patent is subject to a terminal disclaimer.

(21) Appl. No.: 17/095,261

(22) Filed: Nov. 11, 2020

(65) Prior Publication Data

US 2021/0060361 A1 Mar. 4, 2021

Related U.S. Application Data

(63) Continuation of application No. 16/175,224, filed on Oct. 30, 2018, now Pat. No. 10,864,386.

(51) Int. Cl.
| | |
|---|---|
| *A61Q 3/04* | (2006.01) |
| *A61K 8/35* | (2006.01) |
| *A61K 8/34* | (2006.01) |
| *A61K 8/04* | (2006.01) |
| *A61K 8/06* | (2006.01) |
| *A61K 8/37* | (2006.01) |

(52) U.S. Cl.
CPC ............ *A61Q 3/04* (2013.01); *A61K 8/044* (2013.01); *A61K 8/06* (2013.01); *A61K 8/34* (2013.01); *A61K 8/345* (2013.01); *A61K 8/35* (2013.01); *A61K 8/37* (2013.01); *A61K 2800/28* (2013.01); *A61K 2800/5922* (2013.01)

(58) Field of Classification Search
None
See application file for complete search history.

(56) References Cited

U.S. PATENT DOCUMENTS

| 4,032,464 A | 6/1977 | Mausner |
|---|---|---|
| 4,735,798 A | 4/1988 | Bernstein |
| 9,987,212 B2 | 6/2018 | MacNeill et al. |
| 2017/0007516 A1* | 1/2017 | Mercado ............... A61Q 3/04 |

FOREIGN PATENT DOCUMENTS

| CN | 101953769 A | 1/2011 |
|---|---|---|
| CN | 105078801 A | 11/2015 |
| JP | 2014139142 A | 7/2014 |
| TW | 201210624 A | 3/2012 |

OTHER PUBLICATIONS

Gentle Nail Remover, Mintel GNPD, p. 1-2, Published on Aug. 2012.
Tommy Girl Sugar Scrub, Mintel GNPD, p. 1-2, Published on Nov. 2001.
Orange Nail Remover Jelly, Mintel GNPD, p. 1-3, Published on Feb. 2011.
3in1 Remover, Mintel GNPD, p. 1-2, Published on Nov. 2012.
Nail Polish Remover Gel, Mintel GNPD, p. 1-2, Published on Aug. 2007.
Nail Polish Remover Gel, Mintel GNPD, p. 1-3, Published on Jan. 2013.
Nail Polish Remover Gel, Mintel GNPD, p. 1-2, Published on Feb. 2008.
Acetone Solution Nail Polish Remover, Mintel GNPD, p. 1-3, Published on Jun. 2009.
Acetone-Based Nail Polish Remover, Mintel GNPD, p. 1-2, Published on Jul. 2005.

* cited by examiner

*Primary Examiner* — Nannette Holloman
(74) *Attorney, Agent, or Firm* — Oblon, McClelland, Maier & Neustadt, L.L.P.

(57) ABSTRACT

The present invention relates to compositions for removing nail polish that include a C2-C3 monoalcohol, at least about 15% glycerin, and at least about 20% by weight of a C2-C4 alkyl acetate, and combinations thereof. The compositions include less water than glycerin. Methods of using these compositions to remove nail polish and moisturize the hands are also provided.

17 Claims, 2 Drawing Sheets

COMPOSITIONS COMPRISING SOLVENT, A MONOALCOHOL AND GLYCERIN

CROSS-REFERENCE TO RELATED APPLICATIONS

This application is a continuation of and claims the benefit of priority under 35 U.S.C. § 120 from U.S. application Ser. No. 16/175,224, filed Oct. 30, 2018, now allowed, the entire contents of which are incorporated by reference.

FIELD OF THE INVENTION

The present invention relates to compositions and methods for removing nail polish.

DISCUSSION OF THE BACKGROUND

Nail polish compositions are typically designed to provide long-lasting color to nails. Because of the materials used in nail polish compositions to obtain the desired properties, it has proven difficult to remove such nail polish compositions from nails without adversely affecting the nails.

In particular, the inventors have recognized the need to provide efficacious nail polish removal using compositions that include highly efficacious solvents such as acetone and alkyl acetates, yet are capable of providing moisturization and are easy to use.

SUMMARY OF THE INVENTION

The present invention relates to compositions for removing nail polish that include a C2-C3 monoalcohol, at least about 15% glycerin, and at least about 20% by weight of a solvent selected from acetone, a C2-C4 alkyl acetate, and combinations thereof. The compositions include less water than glycerin.

The present invention also relates to methods for removing nail polish from nails and moisturizing the hands of a subject. The method includes applying a composition to the hands and to nails of a subject onto which the nail polish had been previously applied and removing the nail polish from the nails. The compositions include a C2-C3 monoalcohol, at least about 15% glycerin, and at least about 20% by weight of a solvent selected from acetone, a C2-C4 alkyl acetate, and combinations thereof. The compositions include less water than glycerin.

It is to be understood that both the foregoing general description and the following detailed description are exemplary and explanatory only, and are not restrictive of the invention.

DETAILED DESCRIPTION OF THE INVENTION

Figure 1:
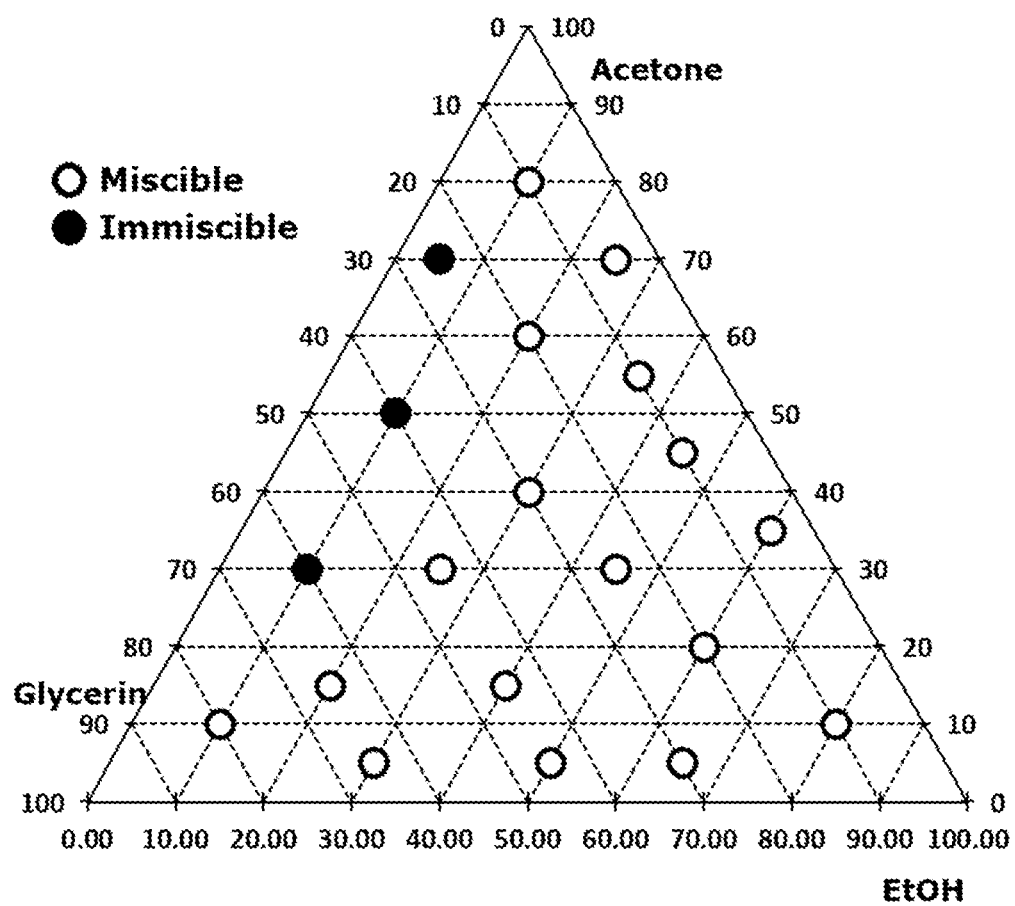
FIG. 1 is a phase diagram using data developed by the inventors, showing relative concentrations of glycerin, acetone and ethanol and a region of miscibility thereof.

As used herein, the expression "at least one" means one or more and thus includes individual components as well as mixtures/combinations. All percentages listed are by weight unless otherwise noted.

Furthermore, all concentrations (and concentration ranges) of glycerin, the C2-C3 monoalcohol, water, acetone, and thickeners in this specification may apply to the entire composition or (when the composition includes multiple phases) or just to a multicomponent solution phase (described herein). For example, unless explicitly stated otherwise when the specification states that glycerin may be present in an amount of about 15% to about 60%, not only does this contemplate that range of glycerin concentration in the composition, but it also contemplates that range of concentration of glycerin in the multicomponent solution phase of a multiphase composition.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

Other than in the operating examples, or where otherwise indicated, all numbers expressing quantities of ingredients and/or reaction conditions are to be understood as being modified in all instances by the term "about," meaning within 10% to 15% of the indicated number, such as within about 5% of the indicated number.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Nail" as used herein includes fingernails as well as toenails.

The compositions, coats and methods of the present invention can comprise, consist of, or consist essentially of the essential elements and limitations of the invention described herein, as well as any additional or optional ingredients, components, or limitations described herein or otherwise useful.

For purposes of the compositions and methods of the present invention where the invention "consists essentially of" the identified ingredients and/or process steps, the two "basic and novel properties" of such compositions and/or methods are "removing nail polish from nails," and "phase stability.

Compositions for Removing Nail Polish

The inventors have found that while glycerin serves as an efficient humectant for moisturizing the skin, glycerin is generally immiscible with acetone and ethyl acetate. However, the inventors have found that certain mixtures of these acetone/alkyl acetate plus C2-C4 monoalcohols and glycerin components are indeed both miscible and capable of removing nail polish. The inventors have surprisingly found this to be the case even for levels of glycerin that are relatively high (at least about 15%).

In accordance with the present invention, compositions for removing nail polish comprising a C2-C3 monoalcohol, glycerin, and a nail polish-removing solvent selected from acetone, a C2-C4 alkyl acetate and combinations thereof are provided. The compositions include at least about 15% glycerin, and at least about 20% by weight of the nail-polish removing solvent selected from acetone, a C2-C4 alkyl acetate, and combinations thereof. Water is optional, but if included, wherein the concentration of water is less than the concentration of glycerin.

Glycerin

In accordance with the present invention, compositions for removing nail polish comprising glycerin (a.k.a., glycerol, glycerine, propanetriol, 1,2,3-Trihydroxypropane or 1,2,3-Propanetriol) are provided. By glycerol, it is meant the polyol compound $C_3H_8O_3$, having the general structure below as well as, in certain embodiments, isomers thereof.

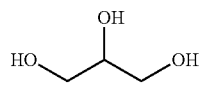

Accordingly, glycerin may be present in the compositions of the present invention in an amount of from about 15%, 20%, or 25% by weight to about 50%, 55%, 60% or 70% by weight. In certain notable embodiments the glycerin is present in a concentration that is from about 15% to about 60%, with all weights being based on the weight of the composition.

C2-C3 Monoalcohol

In accordance with the present invention, compositions for removing nail polish comprising a C2-C3 monoalcohol are provided.

"C2-C3 monoalcohol" means an alcohol having 2 or 3 carbon atoms such as ethanol, propanol, and isopropanol. In certain embodiments the C2-C3 monoalcohol is ethanol.

The C2-C3 monoalcohol is present in the compositions of the present invention in an amount of from about 1%, 10%, 15% or 25% by weight to about 20%, 25%, 30%, 35%, 40% or 65% by weight. In certain other embodiments, the C2-C3 monoalcohol is present in a concentration of at least about 10%. In certain other embodiments the concentration of C2-C3 monoalcohol is present in a concentration of from about 1% to about 65%, such as from about 15% to about 65%, such as from about 20% to about 50%.

Nail-Polish Removing Solvent

In accordance with the present invention, compositions for removing nail polish comprising a nail polish-removing solvent selected from acetone, a C2-C4 alkyl acetate, and combinations (across all relative proportions of acetone and ethyl acetate) thereof. In certain embodiments, the C2-C4 alkyl acetate is ethyl acetate. In yet other embodiments, in order to provide phase compatibility, the compositions are substantially free of alkylene carbonates such as propylene carbonate.

The nail polish-removing solvent may be present in the compositions of the present invention in an amount from about 10%, 20%, 25% or 30% to about 50%, 60%, 70% or 85% by weight. In certain notable embodiments, the nail polish-removing solvent is present from 20% to about 85%.

As discussed, the inventors have further surprisingly identified that sufficiently high levels of glycerin can be beneficially incorporated into compositions including solvents that glycerin is not generally compatible with—acetone/C2-C4 alkyl acetates, even in systems with relatively low amounts of C2-C3 monoalcohol. Accordingly, compositions of the present invention have may ratios by weight of glycerin to C2-C4 monoalcohol that are from 1:1 to 3:1 (in other words ranging from one to three times as much glycerin as C2-C3 monoalcohol). For sake of clarity, by "ratios of glycerin to C2-C4 monoalcohol that are from about 1:1 to about 3:1," for example, it is meant that if the concentration by weight of glycerin is about 15%, then the concentration by weight of C2-C3 monoalcohol is about 5% to about 15% by weight.

According to certain embodiments of the invention, the nail-polish removing solvent is predominantly acetone (>50% by weight acetone as a percentage of all solvents selected from acetone and C2-C4 alkyl acetates in the composition). The inventors have found that the nail-polish removing solvent is predominantly acetone, to enhance removability for compositions with at least about 15% glycerin, it may be desirable for the composition to include up to about 65% by weight of a C2-C3 monoalcohol, about 15% to about 60% by weight of glycerin, and about 20% to about 85% by weight of acetone. The inventors have further found that in order to maintain phase stability it may be desirable to include a level of C2-C3 monoalcohol that is from about 10% to about 65%, such as from about 15% to about 65%. In such embodiments the nail polish-removing solvent may be at least 75% acetone such as about 100% acetone.

According to other certain embodiments of the invention, the nail-polish removing solvent is predominantly C2-C4 alkyl acetate such as ethyl acetate (>50% by weight C2-C4 alkyl acetate as a percentage of all solvents selected from acetone and C2-C4 alkyl acetates in the composition). The inventors have found that the nail-polish removing solvent is predominantly C2-C4 alkyl acetates, to enhance phase stability for compositions with at least about 15% glycerin, it may be desirable for the composition to include from about 25% up to about 75% by weight of a C2-C3 monoalcohol, about 15% to about 70% by weight of glycerin, and about 10% to about 60% by weight of C2-C4 alkyl acetate. In such embodiments the nail polish-removing solvent may be mostly (at least 75%) C2-C4 alkyl acetate (e.g., ethyl acetate) such as about 100% C2-C4 alkyl acetate (e.g., about 0% acetone).

In certain embodiments, compositions of the present invention include C2-C3 monoalcohol, glycerin, and the nail-polish removing solvent such that the concentrations of these components by weight relative to one another are as described in the previous two paragraphs. For example, the composition may include about 60% to 100% by weight of a mixture, where the mixture includes about 65% by weight of a C2-C3 monoalcohol, about 15% to about 60% by weight of glycerin, and about 20% to about 85% by weight of acetone. In this embodiment, the composition further includes 0% to about 40% of additional components which are described below.

In compositions of the present invention, the C2-C3 monoalcohol, glycerin, and nail polish-removing solvent(s) may exist as components of a multicomponent solution phase. In other words, the C2-C3 monoalcohol, glycerin, and nail polish-removing solvent(s) are present in concentrations such that these components are jointly co-soluble in one another.

In certain embodiments, the multicomponent solution phase consists of or consists essentially of the C2-C3 monoalcohol, glycerin, and the nail polish-removing solvent(s). In other embodiments, the multicomponent solution phase includes one more additional components. The one more additional components may, in certain embodiments comprise no more than about 10% by weight of the multicomponent solution phase. The nature of the one or more additional components may vary, but are generally selected from ingredients that are capable of dissolving in a single phase mixture of the C2-C3 monoalcohol, glycerin, and the nail-polish removing solvent. Examples of suitable additional components include fragrances, preservatives, polymeric thickening agents, polar oils, polar waxes, suspending agents, surfactants, emulsifiers, and the like.

Polymeric Thickening Agent

In accordance with the present invention, compositions for removing nail polish comprising at least one thickening agent are provided. Non-limiting examples of thickening agents that may be used according to various embodiments of the present invention include those conventionally used in cosmetics, such as polymers of natural origin and synthetic polymers. For example, nonionic, anionic, cationic, amphiphilic, and amphoteric polymers, and other known rheology modifiers, such as cellulose-based thickeners, may be used.

According to certain embodiments, the thickening agent is an acrylic thickening agent (acrylic thickener) or an acrylamide thickening agent (acrylamide thickener).

"Acrylic thickening agent" or "acrylic thickener" as used herein refers to polymers based upon one or more (meth)acrylic acid (and corresponding (meth)acrylate) monomers or similar monomers.

"Acrylamide thickening agent" or "acrylamide thickener" as used herein refers to polymers based upon one or more acrylamide monomers or similar monomers.

According to certain embodiments, the thickening agent comprises at least one monomer performing a weak acid function such as, for example, acrylic acid, methacrylic acid, itaconic acid, crotonic acid, maleic acid and/or fumaric acid.

According to certain embodiments, the thickening agent comprises at least one monomer performing a strong acid function such as, for example, monomers having a function of the sulfonic acid type or phosphonic acid type, such as 2-acrylamido-2-methylpropane sulfonic acid (AMPS).

According to certain embodiments, the thickening agent may be crosslinked (or branched). Suitable examples of acceptable crosslinking agents include, but are not limited to, methylene bisacrylamide (MBA), ethylene glycol diacrylate, polyethylene glycol dimethacrylate, diacrylamide, cyanomethacrylate, vinyloxyethacrylate or methacrylate, formaldehyde, glyoxal, and compositions of the glycidylether type such as ethyleneglycol diglycidylether, or epoxides.

Suitable acrylic thickeners are disclosed in U.S. patent application publication nos. 2004/0028637 and 2008/0196174, the entire contents of both of which are incorporated herein by reference.

Specific non-limiting examples of suitable thickening agents include homopolymers or copolymers of acrylic or methacrylic acids or the salts thereof and the esters thereof, such as the products sold under the names VERSICOL F or VERSICOL K by Allied Colloid, ULTRAHOLD 8 by Ciba-Geigy, polyacrylates and polymethacrylates such as the products sold under the names LUBRAJEL and NORGEL by Guardian, or under the name HISPAJEL by Hispano Chimica, polyacrylic acids of SYNTHALEN K type, polyacrylamides, copolymers of acrylic acid and of acrylamide sold in the form of the sodium salt thereof, such as under the names RETEN by Hercules, the sodium polymethacrylate such as sold under the name DARVAN 7 by Vanderbilt, and the sodium salts of polyhydroxycarboxylic acids such as sold under the name HYDAGEN F® by Henkel, optionally crosslinked and/or neutralized 2-acrylamido-2-methylpropanesulphonic acid polymers and copolymers, for instance poly(2-acrylamido-2-methylpropanesulphonic acid) such as sold by Clariant under the name HOSTACERIN AMPS (INCI name: ammonium polyacryldimethyltauramide), crosslinked anionic copolymers of acrylamide and of AMPS, e.g. in the form of a water-in-oil emulsion, such as those sold under the name SEPIGEL 305 (INCI name: Polyacrylamide/C13-14 Isoparaffin/Laureth-7) and under the name SIMULGEL 600 (CTFA name: Acrylamide/Sodium acryloyldimethyltaurate copolymer/Isohexa-decane/Polysorbate 80) by SEPPIC, polyacrylic acid/alkyl acrylate copolymers of PEMULEN type, sodium acrylate/sodium acryloyldimethyl taurate such as that sold under the INCI name Sodium Acrylate/Sodium Acryloyldimethyl Taurate Copolymer & Hydrogenated Polydecene & Sorbitan Laurate & Trideceth-6 which is marketed by Lonza, Allendale, N.J., USA under the tradename ViscUpEZ. In certain embodiments, the thickening agent is selected from an acrylamide and a water soluble cellulose polymer (such as hydroxypropylmethylcellulose, ethylcellulose, and/or hydroxypropylcellulose), and combinations thereof.

According to certain embodiments, the thickening agent is a cellulose-based thickener. Suitable cellulose-based compounds include, but are not limited to, cellulose polymers, such as, for example, hydroxyethylcellulose, hydroxypropylcellulose, methylcellulose, and ethylhydroxyethylcellulose. Certain notable cellulose derivatives include hydroxyl-modified cellulose polymers such as Hydroxyethylcellulose, e.g., those having a molecular weight over 500,000 daltons such as NATROSOL 250 HHR and Hydroxypropyl cellulose, e.g., KLUCEL MF—both available from Ashland of Covington, Ky.

According to certain embodiments, the thickening agent is a polysaccharide. In general, polysaccharides may be divided into several categories. Polysaccharides that are suitable for use in the invention may be homopolysaccharides such as fructans, glucans, galactans and mannans or heteropolysaccharides such as hemicellulose. Suitable polysaccharides may be linear polysaccharides such as pullulan or branched polysaccharides such as gum arabic and amylopectin, or mixed polysaccharides such as starch.

The at least one thickening agent may be present in the compositions of the present invention in an amount greater than 0.05% by weight, such as greater than 0.1% by weight, such as greater than 0.5% by weight, such as greater than 1% by weight and may be less than 15% by weight, including all ranges and subranges therebetween such as, for example, from 0.1% to 15%, such as from 0.1% to 10%, such as from 0.5% to 10%, such as from 0.75% to 7.5%, such as from 1% to 5%, etc., with all weights being based on the weight of the composition.

In certain embodiments, the composition may comprise multiple phases. According to one embodiment, the composition comprises two immiscible liquid phases. In particular, the inventors have also further surprisingly identified that particularly when the nail-polish removing solvent is predominantly, mostly or entirely acetone, and when the concentration of acetone is about 15% to about 85%, and the concentration of glycerin is 15% to about 60%, levels of C2-C3 monoalcohol can be maintained from about 0% to about 10% by weight. While in this embodiment, the mixture is immiscible, the mixture can be shaken or agitated and the agitated mixture retains its homogeneity and if tested relatively quickly, still surprisingly shows good nail-polish removal capabilities.

According to certain other embodiments, the composition may comprise a (e.g., a single) multicomponent solution phase and a suspended solid phase that is suspended in the multicomponent solution phase. The suspended solid phase may include any of various ingredients that do not dissolve in the multicomponent solution phase and are capable of being suspended therein. According to certain notable embodiments, the suspended solid phase includes one or more abrasive compounds.

Abrasive Compound

In accordance with the present invention, compositions for removing nail polish comprising at least one abrasive compound (abrasive system) are provided. A "abrasive compound" is a compound capable of providing abrasion or mechanical exfoliation and in accordance with the present invention has one or more of the following characteristics: (1) Surface roughness: particles with irregular edges provide for abrasion; (2) shape: the particles of the abrasive compound may have a non-angular shape such as a disc, oval or sphere; (3) average particle size: in the context of abrasive compounds from mineral origins, shells, seeds micronized fruit kernel powders, and the like. The particles of the abrasive may have a particle size of 1000 microns (μm) or less, such as 500 μm or less, such as 300 μm or less, such as 150 μm or less, such as 75 μm or less, such as, 50 μm or less such as 30 μm or less; and (4) hardness: the abrasive particles may be soft so as to provide for mild abrasion. According to certain embodiments, the abrasive of the present invention has at least two of the above-mentioned properties, such as at least three of the above-mentioned properties, such as all four of the above-mentioned properties. For example—the abrasive compound may be a large spherical material and not hard; or very small, hard, and having an irregular shape. The hardness may be between (inclusive of endpoints) 3-8 (Mohs hardness); or between 40-60 (Shore D hardness) if the compound is a wax or polymer.

The abrasive of the present invention may have at least two of the above-mentioned properties, such as at least three of the above-mentioned properties, and such as all four of the above-mentioned properties.

Suitable non-limiting examples of abrasive compounds include, but are not limited to, water-soluble abrasives such as sugars; and/or water-insoluble abrasives such as ground fruit kernel or shell powders, materials such as perlite, pumice or apricot kernel, coconut scrubs, zeolites, hydrated silica, calcium carbonate, dicalcium phosphate dihydrate, calcium pyrophosphate, alumina, sodium bicarbonate, polylactic acid, spherical waxes (for example, jojoba scrubeads), as well as synthetic polymeric materials such as polyethylene, polypropylene, polyethylene terephthalate, polymethyl methacrylate or nylon.

The at least one abrasive compound may be present in the compositions of the present invention in an amount greater than 0.5% by weight, such as greater than 1% by weight, such as greater than 2.5% by weight, such as greater than 5% by weight such as less than 40% by weight, including all ranges and subranges therebetween such as, for example, from 0.5% to 40%, such as from 1% to 30%, such as from 2.5% to 25%, such as from 5% to 20%, etc., with all weights being based on the weight of the composition. However, it is to be understood that these weight amounts in this paragraph refer to the total amount of abrasive compound present, including those particles which particles of the abrasive compound used in accordance with the present invention which do not have the smoothness, shape, size and/or surface roughness characteristics discussed above.

The suspended solid phase may include other particulate material such as pigments, optical modifiers, tactile modifiers, and the like.

According to other embodiments, compositions of the present invention may also include an inorganic thickening agent. This may be an organoclay (hydrophobically treated clay), a hydrophilic clay, or other inorganic thickener.

According to certain embodiments of the present invention, the compositions for removing nail polish have less than about 10% by weight of water or less than about 5% by weight of water. In certain other embodiments the compositions are "essentially free" of water, or "substantially free" of water. "Essentially free" means that the composition contains less than about 3% of the identified ingredient. "Substantially free" means that the composition contains less than about 2% of the identified ingredient. "Free" means that the composition contains less than 1% of the identified ingredient. A composition containing "no water" contains about 0% of the identified ingredient.

In certain embodiments of the invention are essentially free, substantially free, or free of oils. As used herein, by "oils," it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy)sulfonyl moieties. In certain embodiments, the oil does not include hydroxyl moieties.

Suitable examples of compounds of oils include vegetable oils (glyceryl esters of fatty acids, monoglycerides, diglycerides, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, ethylhexyl hydroxystearate, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

The compositions according to the invention can be manufactured by known processes used generally in the cosmetics or dermatological field.

According to certain embodiments, methods of removing nail polish from nails comprising applying a composition for removing nail polish described above to nails onto which nail polish has been previously applied and removing the nail polish from the nails are provided.

According to certain other embodiments, methods of removing nail polish from nails (and optionally moisturizing hands) include the steps of applying a composition for removing nail polish described above to the hands as well as to the nails onto which nail polish has been previously applied; and removing the nail polish from the nails. The composition may also be rinsed from the hands and nails such as with water. In certain embodiments, compositions of the present invention may be advantageously used without an absorbent pad (otherwise commonly used to remove nail polish from the nails).

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example I(a)—Removability

An experiment was conducted to assess removability of nail polish using twenty compositions including ethanol, acetone, and glycerin. Twenty mixtures of ethanol, glycerin, and acetone were prepared by combining the ingredients in the relative concentrations by weight listed below and mixing on high speed vortex for 10 seconds.

Six mm draw down cards were prepared using ESSIE Russian Roulette nail lacquer available from L'Oreal SA of Paris, France. The cards were allowed to dry for 24 hours.

Mixtures were shaken for 5 seconds and a pipet was filled ⅓ full with mixture and applied to a cotton pad. The pad was folded in half three times, and the card was wiped until the polish was removed, counting the number of strokes needed. The observation was recorded in Table 1, below:

TABLE 1

Nail Polish Removability for Acetone/Ethanol/Glycerin System

| EXAMPLE | Acetone | Ethanol | Glycerin | # of Wipes Required To Remove |
|---|---|---|---|---|
| 1 | 80 | 10 | 10 | 10 |
| 2 | 70 | 25 | 5 | 8 |
| 3 | 70 | 5 | 25 | 9 |
| 4 | 60 | 20 | 20 | 8 |
| 5 | 55 | 35 | 10 | 15 |
| 6 | 50 | 10 | 40 | 5 |
| 7 | 45 | 45 | 10 | 6 |
| 8 | 40 | 30 | 30 | 20 |
| 9 | 35 | 60 | 5 | 8 |
| 10 | 30 | 10 | 60 | 16 |
| 11 | 30 | 25 | 45 | 6 |
| 12 | 30 | 45 | 25 | 14 |
| 13 | 20 | 60 | 20 | 10 |
| 14 | 15 | 40 | 45 | 27 |
| 15 | 15 | 20 | 65 | 58 |
| 16 | 10 | 80 | 10 | 27 |
| 17 | 10 | 10 | 80 | 100+ |
| 18 | 5 | 30 | 65 | 100+ |
| 19 | 5 | 65 | 30 | 79 |
| 20 | 5 | 50 | 45 | 56 |

Example I(b)—Removability

An experiment was conducted to assess removability of nail polish, similarly to Example I (a), using twenty compositions including ethanol, ethyl acetate, and glycerin.

The observations were recorded in Table 2, below:

TABLE 2

Nail Polish Removability for Ethyl Acetate/Ethanol/Glycerin System

| EXAMPLE | Acetone | Ethanol | Glycerin | # of Wipes Required To Remove |
|---|---|---|---|---|
| 1 | 80 | 10 | 10 | 20 |
| 2 | 70 | 25 | 5 | 4 |
| 3 | 70 | 5 | 25 | 4 |
| 4 | 60 | 20 | 20 | 49 |
| 5 | 55 | 35 | 10 | 8 |
| 6 | 50 | 10 | 40 | 40 |
| 7 | 45 | 45 | 10 | 6 |
| 8 | 40 | 30 | 30 | 10 |
| 9 | 35 | 60 | 5 | 20 |
| 10 | 30 | 10 | 60 | 100+ |
| 11 | 30 | 25 | 45 | 10 |
| 12 | 30 | 45 | 25 | 23 |
| 13 | 20 | 60 | 20 | 25 |
| 14 | 15 | 40 | 45 | 60 |
| 15 | 15 | 20 | 65 | 51 |
| 16 | 10 | 80 | 10 | 50 |
| 17 | 10 | 10 | 80 | 38 |
| 18 | 5 | 30 | 65 | 100+ |
| 19 | 5 | 65 | 30 | 70 |
| 20 | 5 | 50 | 45 | 100+ |

However, unlike the removability results for acetone above, the results for immiscible ethyl acetate appear somewhat unreliable as for the acetone system, since after shaking the phases immediately again separate, making it very difficult to isolate a representative composition of the mixture to test for removability.

Example II(a)—Phase Stability

The twenty mixtures mixtures of ethanol, glycerin, and acetone above were prepared as above (in Example I(a) by combining the ingredients in the relative concentrations by weight listed below and mixing on high speed vortex for 10 seconds. The mixtures were evaluated after one hour and twenty-four hours by visually assessing the co-miscibility of the mixtures, looking for visible phase separation or haze upon shaking the ingredients together as an indication of instability. The results are indicated in Table 3, below.

TABLE 3

Phase Stability for Acetone/Ethanol/Glycerin System

| EXAMPLE | Acetone | Ethanol | Glycerin | Miscible (M) or Immiscible (I) |
|---|---|---|---|---|
| 1 | 80 | 10 | 10 | M |
| 2 | 70 | 25 | 5 | M |
| 3 | 70 | 5 | 25 | I |
| 4 | 60 | 20 | 20 | M |
| 5 | 55 | 35 | 10 | M |
| 6 | 50 | 10 | 40 | I |
| 7 | 45 | 45 | 10 | M |
| 8 | 40 | 30 | 30 | M |
| 9 | 35 | 60 | 5 | M |
| 10 | 30 | 10 | 60 | I |
| 11 | 30 | 25 | 45 | M |
| 12 | 30 | 45 | 25 | M |
| 13 | 20 | 60 | 20 | M |
| 14 | 15 | 40 | 45 | M |
| 15 | 15 | 20 | 65 | M |
| 16 | 10 | 80 | 10 | M |

TABLE 3-continued

Phase Stability for Acetone/Ethanol/Glycerin System

| EXAMPLE | Acetone | Ethanol | Glycerin | Miscible (M) or Immiscible (I) |
|---|---|---|---|---|
| 17 | 10 | 10 | 80 | M |
| 18 | 5 | 30 | 65 | M |
| 19 | 5 | 65 | 30 | M |
| 20 | 5 | 50 | 45 | M |

The twenty mixtures of ethanol, glycerin, and ethyl acetate above were prepared as above (in Example I(b)) by combining the ingredients in the relative concentrations by weight listed below and mixing on high speed vortex for 10 seconds. The mixtures were evaluated after one hour and twenty-four hours by visually assessing the co-miscibility of the mixtures, looking for visible phase separation or haze upon shaking the ingredients together as an indication of instability.

TABLE 4

Phase Stability for Ethyl Acetate/Ethanol/Glycerin System

| EXAMPLE | Acetone | Ethanol | Glycerin | Miscible (M) or Immiscible (I) |
|---|---|---|---|---|
| 1 | 80 | 10 | 10 | I |
| 2 | 70 | 25 | 5 | M |
| 3 | 70 | 5 | 25 | I |
| 4 | 60 | 20 | 20 | I |
| 5 | 55 | 35 | 10 | M |
| 6 | 50 | 10 | 40 | I |
| 7 | 45 | 45 | 10 | M |
| 8 | 40 | 30 | 30 | M |
| 9 | 35 | 60 | 5 | M |
| 10 | 30 | 10 | 60 | I |
| 11 | 30 | 25 | 45 | M |
| 12 | 30 | 45 | 25 | M |
| 13 | 20 | 60 | 20 | M |
| 14 | 15 | 40 | 45 | M |
| 15 | 15 | 20 | 65 | I |
| 16 | 10 | 80 | 10 | M |
| 17 | 10 | 10 | 80 | I |
| 18 | 5 | 30 | 65 | M |
| 19 | 5 | 65 | 30 | M |
| 20 | 5 | 50 | 45 | M |

Figure 2:
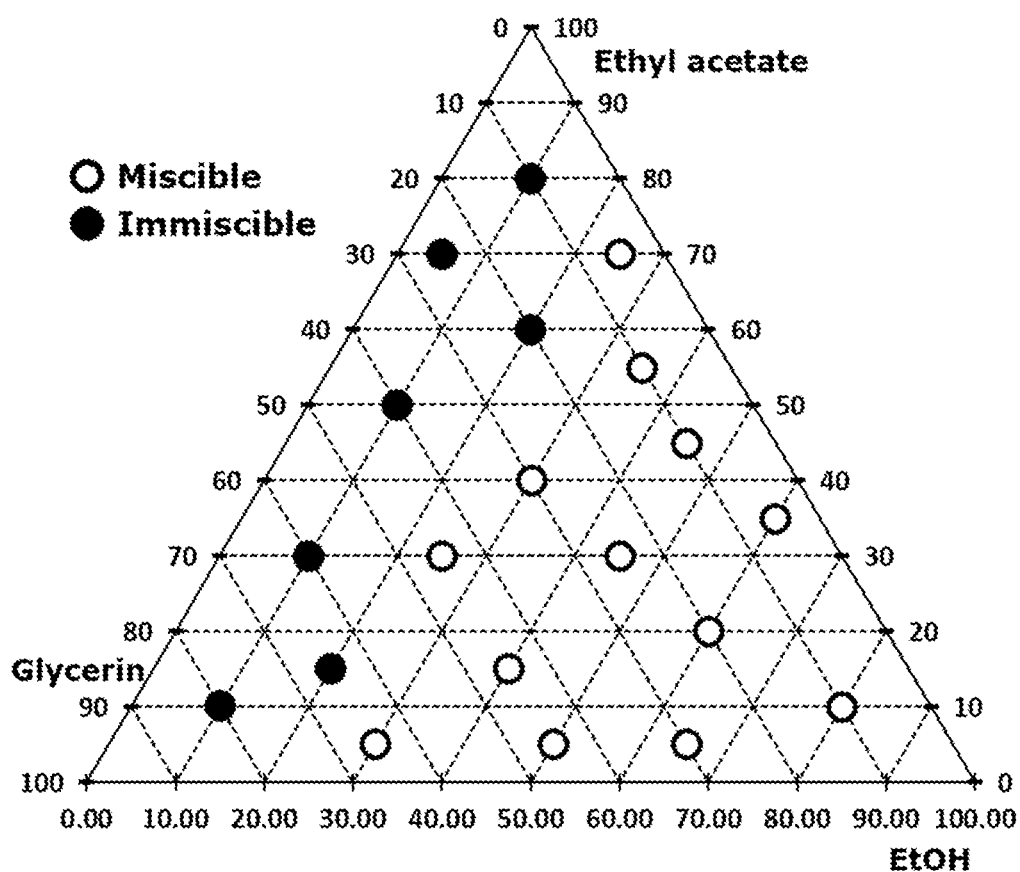
FIG. 2 is a phase diagram using data developed by the inventors, showing relative concentrations of glycerin, ethyl acetate and ethanol and a region of miscibility thereof.

The results are further displayed in FIG. 1 (acetone) and FIG. 2 (ethyl acetate), which are essentially phase diagrams of each set of three components. Open circles indicate miscible mixtures and closed circles indicate immiscible mixtures.

The removability and phase stability results for the acetone system indicate that if one desires to include about 15% or more of glycerin, one should use up to about 65% by weight of ethanol, about 15% to about 60% by weight of glycerin, and about 20% to about 85% acetone to achieve high removability. To work with a single phase system one would use about 10% to about 65% ethanol, whereas to work with a two phase system, one would use 0% to about 10% ethanol.

While the removability data for ethyl acetate is unreliable, the phase stability results for the ethyl acetate system show that if one desires to include about 15% or more of glycerin, then it may be desirable for the composition to include from about 25% up to about 75% by weight of a C2-C3 monoalcohol, about 15% to about 70% by weight of glycerin, and about 10% to about 60% by weight of C2-C4 alkyl acetate.

What is claimed is:

1. A composition for removing nail polish comprising a mixture of:
   from about 25% to about 75% by weight of C2-C3 monoalcohol,
   from about 15% to about 70% of glycerin, and
   from about 10% to about 60% by weight of C2-C4 alkyl acetate: and
   wherein the composition optionally comprises water, wherein the concentration of glycerin in the composition is greater than the concentration of water in the composition.

2. The composition of claim 1, wherein the composition has less than about 5% by weight of water.

3. The composition of claim 1, wherein the composition is essentially free of water.

4. The composition of claim 1, wherein the glycerin and C2-C3 monoalcohol are present in a glycerin and C2-C3 monoalcohol ratio by weight of about 1:1. to 3:1.

5. The composition of claim 1, wherein the glycerin and C2-C3 monoalcohol are present in a glycerin and C2-C3 monoalcohol ratio by weight of about 1.5:1.to 3:1.

6. The composition of claim 1 comprising a multicomponent solution phase of said mixture and a suspended solid phase suspended in the multicomponent solution phase.

7. The composition of claim 6 wherein the suspended solid phase includes an abrasive.

8. The composition of claim 6, wherein the abrasive is water soluble.

9. The composition of claim 6, wherein the multicomponent solution phase comprises the C2-C3 monoalcohol, the glycerin, and the C2-C4 alkyl acetate, and the multicomponent solution phase further comprises one or more additional components.

10. The composition of claim 9, wherein the one or more additional components comprise no more than about 10% by weight of the multicomponent solution phase.

11. The composition of claim 9, wherein the one or more additional ingredients comprise one or more ingredients selected from a group consisting of a polymeric thickening agent, a fragrance, and water.

12. The composition of claim 1 wherein the composition has less than about 5% oil.

13. The composition of claim 1 wherein the C2-C3 monoalcohol, glycerin, and the C2-C4 alkyl acetate, collectively comprise at least about 75% of the composition.

14. The composition of claim 1, wherein the C2-C4 alkyl acetate is ethyl acetate.

15. The composition of claim 14, wherein the concentration by weight of the C2-C3 monoalcohol in the composition is about 25% to about 75% by weight, wherein the concentration by weight of glycerin in the composition is about 15% to about 70% by weight, and the concentration by weight of ethyl acetate in the composition is about 10% to about 60% by weight.

16. A method of removing nail polish from nails and moisturizing the hands of a subject, comprising;
   applying the composition of claim 1 to hands and to nails of a subject onto which the polish had been previously applied; and
   removing the nail polish from the nails.

17. The composition of claim 1, wherein C2-C4 alkyl acetate is present in an amount of from about 20% to about 60% by weight.

* * * * *